United States Patent [19]

Elslager

[11] 4,391,809
[45] Jul. 5, 1983

[54] METHODS FOR TREATING PSORIASIS

[75] Inventor: Edward F. Elslager, Ann Arbor, Mich.

[73] Assignee: Warner-Lambert Company, Ann Arbor, Mich.

[21] Appl. No.: 206,596

[22] Filed: Nov. 13, 1980

Related U.S. Application Data

[63] Continuation of Ser. No. 84,944, Oct. 15, 1979, abandoned.

[51] Int. Cl.³ .......................................... A61K 31/505
[52] U.S. Cl. .................................................... 424/251
[58] Field of Search ........................................ 424/251

[56] References Cited

FOREIGN PATENT DOCUMENTS 1345502 1/1974 United Kingdom .

Primary Examiner—Jerome D. Goldberg
Attorney, Agent, or Firm—Ronald A. Daignault

[57] ABSTRACT

Methods for treating psoriasis by administering 2,4-diamino-5-methyl-6-[(3,4,5-trimethoxyanilino)methyl]-quinazoline, 2,4-diamino-5-chloro-6-[(3,4-dichloroanilino)methyl]-quinazoline or a pharmaceutically acceptable acid-addition salt thereof.

5 Claims, No Drawings

METHODS FOR TREATING PSORIASIS

This is a continuation of application Ser. No. 84,944 filed Oct. 15, 1979, now abandoned.

SUMMARY AND DETAILED DESCRIPTION

The present invention relates to methods for treating psoriasis in mammals, such as dogs, horses, sheep, etc., by administering 2,4-diamino-5-methyl-6-[(3,4,5-trimethoxyanilino)methyl]quinazoline, 2,4-diamino-5-chloro-6-[(3,4-dichloroanilino)methyl]quinazoline or a pharmaceutically acceptable acid-addition salt thereof.

The term "pharmaceutically acceptable acid-addition salt" is intended to mean any salt form that is prepared from a relatively non-toxic acid, such as the hydrochloride, sulfate, phosphate, benzoate, acetate, citrate, tartrate, etc.

In addition, 2,4-diamino-5-methyl-6-[(3,4,5-trimethoxyanilino)methyl]quinazoline, 2,4-diamino-5-chloro-6-[(3,4-dichloroanilino)methyl]quinazoline and their pharmaceutically acceptable acid-addition salts can exist in anhydrous forms as well as in solvated (such as an acetate, hydrates, etc.) forms. In general, the hydrated forms and the solvated forms with pharmaceutically acceptable solvents are equivalent to the anhydrous or unsolvated form for the purposes of the invention and are intended to be within the scope of this invention.

While 2,4-diamino-5-methyl-6-[(3,4,5-trimethoxyanilino)methyl]quinazoline, 2,4-diamino-5-chloro-6-[(3,4-dichloroanilino)methyl]quinazoline or their acid-addition salts may be administered orally with the dosage adjusted for the type of psoriasis and tolerances of the individual patient; the parenteral routes, especially the intravenous route, are most preferred. The usual mammalian dosage range for a 70 kg human subject is from 5 to 500 mg per day (0.07 mg to 7.1 mg per kg of weight per day), preferably 15 to 120 mg per day (0.2 mg to 1.7 mg per kg of weight per day), optionally in divided portions. Therapeutic agents of this type are generally prescribed for a specific time span, such as for a five day period depending upon the disease state being treated.

The above employed pharmaceutical compositions are produced by formulating the active compound in dosage unit form with a pharmaceutical carrier. Some examples of dosage unit forms are tablets, capsules, pills, powders, aqueous and non-aqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present.

I claim:

1. A method for treating psoriasis in mammals which comprises administering an antipsoriatic-effective amount of 2,4-diamino-5-methyl-6-[(3,4,5-trimethoxyanilino)methyl]quinazoline, 2,4-diamino-5-chloro-6-[(3,4-dichloroanilino)methyl]quinazoline or a pharmaceutically acceptable salt thereof, to a mammal in need of said treatment.

2. The method of claim 1 wherein 0.07 mg to 7.1 mg/kg of weight per day of said compound is administered.

3. The method of claim 1 wherein said compound is 2,4-diamino-5-methyl-6-[(3,4,5-trimethoxyanilino)methyl]quinazoline monoacetate.

4. The method of claim 1 wherein said compound is 2,4-diamino-5-chloro-6-[(3,4-dichloroanilino)methyl]quinazoline monoacetate.

5. The method defined in claim 1 wherein said mammal is a human.

* * * * *